United States Patent [19]

Hidaka et al.

[11] 4,125,730
[45] Nov. 14, 1978

[54] PREPARATION OF -AMINOALKANOIC ACID ARYLAMIDES

[75] Inventors: Hiroyoshi Hidaka, Corony-Kosha 1-24, 1044-1, Syona-cho, Kasugai-shi, Aichi-Ken; Ikuo Matsumoto; Yoshiaki Ito, both of Tokyo; Nobuo Aoki, 263-59, Yamamoto-Cho, Utsunomiya-shi, Tochigi-Ken, all of Japan

[73] Assignees: Banyu Pharmaceutical Co., Ltd., Tokyo; Hiroyoshi Hidaka, Aichi; Nobuo Aoki, Tochigi, all of Japan

[21] Appl. No.: 621,408

[22] Filed: Oct. 10, 1975

[30] Foreign Application Priority Data

Aug. 22, 1975 [JP] Japan .................. 50-101124

[51] Int. Cl.² .............. A61K 31/165; A61K 31/245; C07C 103/50; C07C 69/78
[52] U.S. Cl. ................. 560/37; 260/562 N; 260/562 R; 260/562 P; 424/310; 424/324
[58] Field of Search .......... 260/562 N, 562 R, 562 P, 260/471 R; 560/37

[56] References Cited

U.S. PATENT DOCUMENTS

| 2,520,153 | 8/1950 | Lawson et al. | 260/562 N X |
| 2,912,460 | 11/1959 | Ehrhart et al. | 260/562 N |
| 2,948,736 | 8/1960 | Martin | 260/562 N X |
| 3,340,298 | 9/1967 | Wismayr et al. | 260/562 N |
| 3,478,056 | 11/1969 | Schmutz et al. | 260/562 N X |
| 3,786,092 | 1/1974 | Soldati et al. | 260/562 P X |
| 3,812,147 | 5/1974 | Adams et al. | 260/562 N X |
| 3,931,314 | 1/1976 | Greve et al. | 260/562 N |
| 3,943,172 | 3/1976 | Vanhoof et al. | 260/562 N X |

OTHER PUBLICATIONS

Wimeholt et al., J. Labelled Compds. 6, 53(1970) Abstract #389, Theilheimer, Synthesis of Org. Compds. Semikolennykh et al., Med. Prom. SSSR 19(10), 15(1965), Abstr. #409, Theilheimer, Synthesis of Org. Compds.

Primary Examiner—Winston A. Douglas
Assistant Examiner—Thomas A. Waltz
Attorney, Agent, or Firm—Oblon, Fisher, Spivak, McClelland & Maier

[57] ABSTRACT

ω-Aminoalkanoic acid arylamides having the formula:

$R'(CH_2)_n CONHR$ wherein R represents phenyl or naphthyl which can be substituted by halogen, nitro, alkyl, alkoxy, hydroxyl, acetoamino or alkoxycarbonyl; R' represents amino or acylated amino; and $n$ is an integer of 4–8, exhibit blood platelet aggregation inhibiting effects.

3 Claims, No Drawings

PREPARATION OF -AMINOALKANOIC ACID ARYLAMIDES

DETAILED DESCRIPTION OF THE INVENTION

The present invention relates to ω-aminoalkanoic acid arylamides having the formula $$R'(CH_2)_n CONHR \qquad (I)$$

wherein R respresents phenyl or naphthyl which can be substituted by halogen, nitro, alkyl, alkoxyl, hydroxyl, acetoamino or alkoxycarbonyl; R' represents amino or acylated amino; and n is an integer of 4–8.

The compounds having formula (I) can be produced by reacting a ω-aminoalkanoic acid having the formula $$R'(CH_2)_n COOH \qquad (II)$$

wherein R' and n are defined as above or a functional derivative thereof with an aromatic amine having the formula $$RNH_2 \qquad (III)$$

wherein R is defined as above to produce the corresponding alkanoic acid arylamide. If necessary, the protective acyl group is removed from the amino group.

The ω-aminoalkanoic acids of formula (II) used in the invention include δ-aminovalerianic acid, ε-aminocaproic acid, β-aminoenathic acid, η-aminocaprylic acid, θ-aminopelargonic acid, ε-aminocapronic acid and the like. The amino group of the ω-aminoalkanoic acid can be protected with a suitable protective group including acetyl, phthaloyl, carbobenzoxyl and the like. Suitable functional derivatives of the ω-aminoalkanoic acids include acid halides such as acid chlorides and acid bromides; acid esters, acid anhydrides and mixed acid anhydrides of the ω-aminoalkanoic acid and another acid such as chlorocarbonic ester. Suitable aromatic amines having the formula (II) include o-chloroaniline, m-chloroaniline, p-chloroaniline, p-bromoaniline, p-nitroaniline, p-toluidine, 2,6-xylidine, 2-amino-6-chlorotoluene, p-anisidine, p-aminophenol, p-aminoacetoanilide, ethyl p-aminobenzoate, aniline, β-naphthylamine and the like. It is also possible to use arylamine derivatives which form an aromatic amine in the reaction, such as phosazo derivatives produced by the reaction of an aromatic amine with phosphorous trichloride, instead of the aromatic amine.

In the process of the invention, the ω-aminoalkanoic acid or the functional acid derivative (II) is admixed with the aromatic amine (III) preferably in the presence of a solvent and reacted. When an acid halide is used, it is possible to add an alkaline compound such as pyridine, triethylamine, or the like as a dehydrohalogenating agent to remove hydrogenhalide from the reaction. It is possible to remove hydrogenhalide gas from the reaction system by heating, or a similar means. The solvent is removed and the residue is treated by conventional methods to separate the product. The removal of the protective acyl group from the compound can be performed by any conventional method.

The molar ratio of the aromatic amine to the ω-aminoalkanoic acid or the functional derivative thereof is preferably in the range of 0.5–20, especially 1–10. The ratio of the solvent to the ω-aminoalkanoic acid or the functional derivative thereof is in the range of 2–100. The reaction temperature can be in the range of −20° C. to the boiling point of the solvent. It is preferable to convert the ω-aminoalkanoic acid to a functional derivative thereof, especially to the corresponding ω-aminoalkanoic acid halide in a solvent by adding a halogenating agent such as thionyl chloride, phosphorus pentachloride, phosphorus trichloride, phosphorus oxychloride or sulfuryl chloride to the acid. The resulting ω-aminoalkanoic acid halide is usually used for the reaction with the aromatic amine without separating the acid halide from the halogenating reaction medium. In this case, the amino group of the ω-aminoalkanoic acid halide is usually protected as the hydrochloride even though a protective group is not bonded. In the reaction of an ω-aminoalkanoic acid halide with an aromatic amine, it is preferable to remove hydrogen halide by adding an alkaline material such as pyridine, triethylamine or the like, to the reaction mixture or by vaporizing hydrogen halide by heating the reaction mixture. It is preferable to remove the solvent before purification. When a protective group is bonded to the amino group of the ω-aminoalkanoic acid, the protective group can be removed by any conventional method.

It has been found that the compounds having formula (I) have a blood platelet aggregation inhibiting effect, and are therefore, preventive and therapeutic medicines for thrombosis in the encephalo-and cardio-vascular systems.

Having generally described this invention, a further understanding can be obtained by reference to certain specific examples which are provided herein for purposes of illustration only and are not intended to be limiting unless otherwise specified.

In order to study the blood platelet aggregation inhibiting effects of the compounds of the invention, a platelet rich plasma is prepared by centrifugal separation of a mixture of fresh human blood and a 3.8% solution of sodium citrate in a ratio of 9:1. The effects of the compounds on the blood platelet aggregation induced by collagen, adenosine diphosphate (ADP), epinephrine, thrombin, and the like are then studied. Blood platelet aggregation can be tested by the Aggregometer (manufactured by Bryston Co., Canada) to measure variation in light transmittance of the solution to be tested. The light transmittance increases in proportion to the degree of aggregation of the blood platelets. The light transmittance of blood plasma from which blood platelets are separated by centrifugal separation is rated as 100 and the light transmittance of platelet rich plasma is rated as 0. The light transmittance which increases upon aggregation is shown as aggregation rate (%). The relative aggregation rate (%) is obtained by dividing the aggregation rate by the aggregation rate of a control sample which has replaced the inhibitor compound by a buffered isotonic sodium chloride solution. The inhibition rate (%) for blood platelet aggregation by the active compound is obtained by subtracting the relative aggregation rate from 100.

Collagen is prepared by dispersing 300 mg of insoluble collagen (manufactured by Sigma Co.) in 15 ml of an isotonic sodium chloride solution and removing the rough particles by centrifugal sedimentation. ADP is prepared by dissolving ADP in an isotonic sodium chloride solution in concentrations of $3.7 \times 10^{-4}$ M and maintaining the solution in a frozen condition. Immediately prior to use the frozen solution is thawed and diluted with an 8 times volume of an isotonic sodium chloride solution. Epinephrine is prepared by diluting a 1 mg/ml adrenaline solution (manufactured by Sankyo K.K.) with 20 times the volume of an isotonic sodium chloride solution. Thrombin is prepared by dissolving 500 units of human-thrombin (manufactured by Midori Jyuji K.K.) in 2 ml of 50% glycerin and maintaining the solution at −20° C. and then diluting it with 20 times the volume of an isotonic sodium chloride solution. The results of the blood platelet aggregation tests using collagen are shown in the following Table. Compounds A–H used in the tests are shown in the following examples.

Table

| Test conditions | Test Compound | Final concentration (M) | Aggregation rate (%) | Relative aggregation rate (%) | Inhibition rate (%) |
|---|---|---|---|---|---|
| | Control | 4.5 | 76 | 100 | |
| Collagen 8 μl | Compound E | $4.5 \times 10^{-4}$ | 36.5 | 48 | 52 |
| number of blood | Compound A | " | 0 | 0 | 100 |
| platelets | " | $3.4 \times 10^{-4}$ | 0 | 0 | 100 |
| $33.1 \times 10^4$/c.mm | " | $1.1 \times 10^{-4}$ | 19.8 | 26 | 74 |
| | " | $5.7 \times 10^{-5}$ | 31 | 41 | 59 |
| Collagen 10 μl | Control | | 68 | 100 | |
| number of blood | | | | | |
| platelets | Compound E | $9 \times 10^{-4}$ | 63 | 93 | 7 |
| $40 \times 10^4$/c.mm | Compound D | " | 57 | 84 | 16 |
| | Control | | 67 | 100 | |
| Collagen 8 μl | Compound B | $1.1 \times 10^{-4}$ | 15 | 23 | 77 |
| number of blood | " | " | 1 | 2 | 98 |
| platelets | " | $5.7 \times 10^{-5}$ | 37.5 | 56 | 44 |
| $28 \times 10^4$/c. mm | Compound C | $1.1 \times 10^{-4}$ | 62 | 92 | 8 |
| | Compound G | " | 66 | 99 | 0 – 1 |
| | Compound F | " | 63 | 94 | 6 |
| Collagen 8 μl | Control | | 85.5 | 100 | |
| number of blood | Compound H | $1.4 \times 10^{-4}$ | 7.6 | 8.9 | 91 |
| platelets | " | $9 \times 10^{-5}$ | 49.7 | 58 | 42 |
| $34 \times 10^4$/c.mm | " | $3 \times 10^{-5}$ | 83.6 | 98 | 2 |

Product disclosed:
Compound A ..... Example 4      Compound B ..... Example 7
Compound C ..... Example 8      Compound D ..... Example 9
Compound E ..... Example 10     Compound F ..... Example 11
Compound G ..... Example 16     Compound H ..... Example 17

As is clear from the results in the table, compounds A, B and H are the most effective in inhibiting blood platelet aggregation. In the final concentration of $5.7 \times 10^{-5}$ M, blood platelet aggregation by collagen was inhibited in amounts of about 40–60%. It was found that the inhibiting effect increases in a manner directly proportional to increasing length of time the compound is in contact with the blood platelets, the smaller the number of blood platelets and the smaller the amount of collagen. The compounds of the invention exhibit the same blood platelet aggregation inhibiting effect in the instances when aggregation of the platelets is induced by epinephrine or thrombin. The compounds of the invention are not effective to primary aggregation by ADP, however they are very effective to secondary aggregation by ADP. Accordingly, it is believed that the compounds of the invention inhibit irreversible aggregation which is caused by the reaction of the various discharged amines and the coagulation promoter with the morphologic variation of the blood platelets which result from various stimulants.

Effects of the compounds on blood vessels was examined by using isolated rabbit aorta in Rock's solution at 37° C. The isolated rabbit aorta is significantly relaxed in the presence of a $1 \times 10^{-4}$ M solution of the compounds.

EXAMPLE 1

A 0.9 g amount of δ-aminovalerianic acid was suspended in 10 ml of 1,2-dichloroethane, and then a solution of 0.935 g of thionyl chloride in 10 ml of 1,2-dichloroethane and 0.2 ml of dimethylformamide was added to the suspension. The mixture was stirred at room temperature for 2 hours to dissolve the reactants completely. A solution of 0.675 g of p-chloraniline in 20 ml of 1,2-dichloroethane was added to the solution and the mixture was vigorously stirred at room temperature for about 30 minutes to form a slurry. The slurry was heated for 2 hours under reflux until the evolution of hydrogenchloride gas was finished. After cooling the slurry, the precipitate was filtered and was recrystallized from ethanol whereby 0.83 g of the following compound as colorless needle-like crystals having a melting point of 183°–184° C. (yield 60%) was obtained.

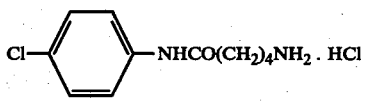

| Elemental analysis: $C_{11}H_{16}N_2OCl_2$ | | | |
|---|---|---|---|
| | C | H | N |
| Calculated (%) | 50.20 | 6.13 | 10.64 |
| Found (%) | 50.18 | 6.17 | 10.64 |

EXAMPLE 2

A 3.6 g amount of δ-aminovalerianic acid was suspended in 35 ml of 1,2-dichloroethane, and then a solution of 3.66 g of thionyl chloride in 30 ml of 1,2-dichlorethane and 0.55 ml of dimethylformamide was added to the suspension. The mixture was stirred at room temperature for 2 hours to dissolve the reactants completely. A solution of 2.69 g of m-chloroaniline in 100 ml of 1,2-dichloroethane was added to the solution and the mixture was stirred at room temperature for about 30 minutes to form a slurry. The slurry was heated for 4 hours under reflux with stirring. After cooling the slurry, the precipitate was filtered and was recrystallized from ethanol whereby 4.3 g of the following compound as colorless needle-like crystals having a melting point of 154°-155° C. (yield 77.6%) were obtained.

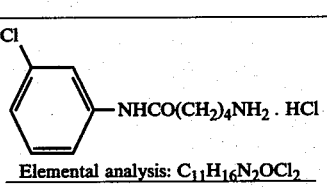

| | C | H | N |
|---|---|---|---|
| Calculated: (%) | 50.37 | 6.14 | 10.67 |
| Found (%): | 50.20 | 6.13 | 10.64 |

Elemental analysis: $C_{11}H_{16}N_2OCl_2$

EXAMPLE 3

A 3.90 g amount of δ-aminovalerianic acid hydrochloride was suspended in 40 ml of 1,2-dichloroethane, and then a solution of 3.96 g of thionyl chloride in 40 ml of 1,2-dichloroethane and 0.6 ml of dimethylformamide was added to the suspension. The mixture was stirred at room temperature for 2 hours to dissolve the reactants completely. A solution of 3.93 g of p-bromoaniline in 80 ml of 1,2-dichloroethane was added to the solution and the mixture was stirred at room temperature for about 30 minutes to form a slurry. The slurry was heated for 3 hours under reflux conditions. After cooling the slurry, the precipitate was filtered and was recrystallized from ethanol whereby 3.65 g of the following compound as colorless needle-like crystals having a melting point of 186°-187° C. (yield 52.3%) were obtained.

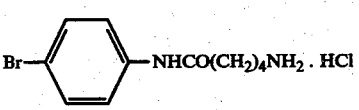

Elemental Analysis: $C_{11}H_{16}N_2OBrCl$

| | C | H | N |
|---|---|---|---|
| Calculated (%) | 42.98 | 5.12 | 9.19 |
| Found (%) | 42.95 | 5.24 | 9.11 |

EXAMPLE 4

A 1.31 g amount of ε-aminocaproic acid was suspended in 20 ml of 1,2-dichloroethane, and then a solution of 1.31 g of thionyl chloride in 10 ml of 1,2-dichloroethane and 0.2 ml of dimethylformamide was added to the suspension. The mixture was stirred at room temperature for 1 hour, and further shaken at 40°-45° C. for 1 hour to dissolve the reactants completely. A solution of 1.27 g of p-chloroaniline in 20 ml of 1,2-dichloroethane was added to the solution and the mixture was vigorously stirred at room temperature to form a slurry. The slurry was heated and stirred for 3 hours under reflux until the evolution of hydrogenchloride gas ceased. After cooling the slurry, the precipitate was filtered and was recrystallized from ethanol whereby 2.6 g of the following compound as colorless prismatic crystals having a melting point of 191°-192° C. (yield 94%) were obtained.

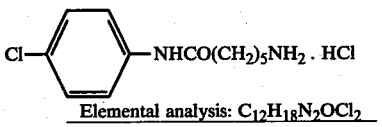

(A)

Elemental analysis: $C_{12}H_{18}N_2OCl_2$

| | C | H | N |
|---|---|---|---|
| Calculated (%) | 51.99 | 6.54 | 10.10 |
| Found (%) | 51.99 | 6.75 | 9.98 |

EXAMPLE 5

The process of Example 4 was repeated except that 1.65 g ethyl p-aminobenzoate was used instead of p-chloroaniline, and the product was recrystallized from ethanol after washing the same with acetone whereby 2.5 g of the following compound as colorless prismatic crystals having a melting point of 177°-178° C. (yield 79.5%) were obtained.

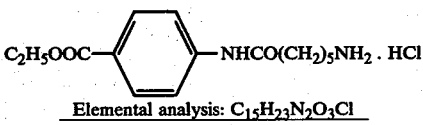

Elemental analysis: $C_{15}H_{23}N_2O_3Cl$

| | C | H | N |
|---|---|---|---|
| Calculated (%) | 57.22 | 7.36 | 8.90 |
| Found (%) | 57.46 | 7.40 | 8.90 |

EXAMPLE 6

The process of Example 4 was repeated except that 1.42 g of 2-amino-6-chlorotoluene was used instead of p-chloroaniline and the product was recrystallized from ethanol after washing the same with acetone, whereby 2.4 g of the following compound as colorless needle-like crystals having a melting point of 166°-167° C. (yield 82.5%) were obtained.

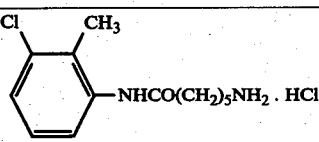

Elemental analysis: $C_{13}H_{20}N_2OCl_2$

| | C | H | N |
|---|---|---|---|
| Calculated (%) | 53.61 | 6.92 | 9.62 |
| Found (%) | 53.88 | 6.99 | 9.55 |

EXAMPLE 7

The process of Example 4 was repeated except that 1.43 g of β-naphthylamine were used instead of p-chloroaniline, and the product was recrystallized from water, whereby 2.3 g of the following compound as colorless needle-like crystals having a melting point of 199°-200° C. (yield 78.8%) were obtained.

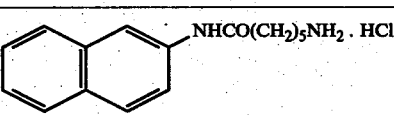

(B)

Elemental analysis: $C_{11}H_{16}N_2OCl_2$

| | C | H | N |
|---|---|---|---|
| Calculated (%) | 65.33 | 7.23 | 9.57 |

(B)

[Structure: naphthalene-NHCO(CH₂)₅NH₂·HCl]

Elemental analysis: $C_{11}H_{16}N_2OCl_2$

| | C | H | N |
|---|---|---|---|
| Found (%) | 65.19 | 7.41 | 9.70 |

The process of Example 4 was repeated except that 1.27 g of m-chloroaniline was used instead of p-chloroaniline and the product was recrystallized from ethanol-ether, whereby 2.1 g of the following compound as colorless needle-like crystals having a melting point of 112°–113° C. (yield 80%) were obtained.

(C)

[Structure: m-Cl-C₆H₄-NHCO(CH₂)₅NH₂·HCl]

Elemental Analysis: $C_{12}H_{18}N_2OCl_2$

| | C | H | N |
|---|---|---|---|
| Calculated (%) | 51.99 | 6.54 | 10.11 |
| Found (%) | 51.72 | 6.59 | 10.14 |

EXAMPLE 9

The process of Example 4 was repeated except that 1.27 g of o-chloroaniline were used instead of p-chloroaniline and the product was recrystallized from ethanol-acetone whereby 1.72 g of the following compound as colorless plate-like crystals having a melting point of 132°–133° C. (yield 62%) were obtained.

(D)

[Structure: o-Cl-C₆H₄-NHCO(CH₂)₅NH₂ HCl]

Elemental Analysis: $C_{12}H_{18}N_2OCl_2$

| | C | H | N |
|---|---|---|---|
| Calculated (%) | 51.99 | 6.54 | 10.10 |
| Found (%) | 52.08 | 6.66 | 10.02 |

EXAMPLE 10

The process of Example 4 was repeated except that 0.93 g of aniline was used instead of p-chloroaniline and the product was recrystallized from ethanol-isopropyl ether whereby 2.25 g of the following compound as colorless plate-like crystals having a melting point of 175°–176° C. (yield 92.5%) were obtained.

(E)

[Structure: C₆H₅-NHCO(CH₂)₅NH₂·HCl]

Elemental analysis: $C_{12}H_{19}N_2OCl$

| | C | H | N |
|---|---|---|---|
| Calculated (%) | 59.37 | 7.89 | 11.54 |
| Found (%) | 59.40 | 7.92 | 11.49 |

EXAMPLE 11

The process of Example 4 was repeated except that 1.07 g of p-toluidine was used instead of the p-chloroaniline and the product was recrystallized from ethanol-isopropyl ether whereby 2.08 g of the following compound as needle-like crystals having a melting point of 183°–184° C. (yield 81.2%) were obtained.

(F)

[Structure: CH₃-C₆H₄-NHCO(CH₂)₅NH₂·HCl]

Elemental analysis: $C_{12}H_{21}N_2OCl$

| | C | H | N |
|---|---|---|---|
| Calculated (%) | 60.80 | 8.24 | 10.91 |
| Found (%) | 61.05 | 8.20 | 10.93 |

EXAMPLE 12

The process of Example 4 was repeated except that 1.21 g of 2,6-xylidine were used instead of p-chloroaniline and the product was recrystallized from ethanol-isopropyl ether whereby 1.3 g of the following compound as colorless needle-like crystals having a melting point 149°–151° C. (yield 48%) were obtained.

[Structure: 2,6-dimethylphenyl-NHCO(CH₂)₅NH₂·HCl]

Elemental analysis: $C_{14}H_{23}N_2OCl$

| | C | H | N |
|---|---|---|---|
| Calculated (%): | 62.09 | 8.56 | 10.35 |
| Found (%): | 61.44 | 9.21 | 9.61 |

EXAMPLE 13

A 1.31 g amount of ε-aminocaproic acid was suspended in 10 ml of 1,2-dichloroethane and then a solution of 1.31 g of thionyl chloride in 10 ml of 1,2-dichloroethane and 0.2 ml of dimethylformamide was added to the suspension. The mixture was stirred at room temperature for 1 hour and then was further shaken at 40°–45° C. for 1 hour to dissolve the reactants completely. A solution of 1.5 g of p-aminoacetanilide in 10 ml of dimethylformamide and 1.2 g triethylamine was added to the solution, and the mixture was stirred for 2 hours. Then the reaction mixture was diluted with 1,2-dichloroethane. The resulting precipitate was filtered and recrystallized from methanol whereby 2.2 g of the following compound as colorless needle-like crystals having a melting point of 239° C. (yield 48.8%) were obtained.

[Structure: CH₃CONH-C₆H₄-NHCO(CH₂)₅NH₂·HCl·½ H₂O]

Elemental analysis: $C_{14}H_{22}N_3OCl \cdot \tfrac{1}{2} H_2O$

| | C | H | N |
|---|---|---|---|
| Calculated (%): | 54.54 | 7.36 | 13.63 |

-continued

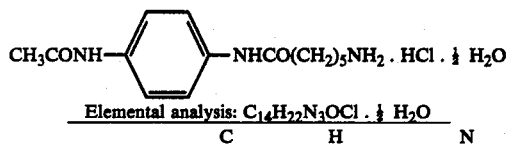

Elemental analysis: $C_{14}H_{22}N_3OCl \cdot \frac{1}{2} H_2O$

|  | C | H | N |
|---|---|---|---|
| Found (%): | 54.42 | 7.59 | 13.54 |

EXAMPLE 14

The process of Example 13 was repeated except that 1.09 g of p-aminophenol was used instead of p-aminoacetanilide and the product was recrystallized from ethanol whereby 2 g of the following compound as colorless prismatic crystals having a melting point of 198°–201° C. (yield 77.3%) were obtained.

HO—⟨C₆H₄⟩—NHCO(CH₂)₅NH₂ · HCl

Elemental analysis: $C_{12}H_{19}N_2OCl$

|  | C | H | N |
|---|---|---|---|
| Calculated (%): | 55.70 | 7.40 | 10.83 |
| Found (%): | 55.58 | 7.55 | 10.87 |

EXAMPLE 15

The process of Example 13 was repeated except that 1.38 g of p-nitroaniline was used instead of p-aminoacetanilide and the product was recrystallized from ethanol whereby 1.9 g of the following compound as pale yellow needle-like crystals having a melting point of 229° C. (decomposition) (yield 66.3%) were obtained.

O₂N—⟨C₆H₄⟩—NHCO(CH₂)₅NH₂ · HCl

Elemental analysis: $C_{12}H_{18}N_3O_3Cl$

|  | C | H | N |
|---|---|---|---|
| Calculated (%): | 50.09 | 6.30 | 14.60 |
| Found (%): | 50.02 | 6.40 | 14.64 |

EXAMPLE 16

The process of Example 13 was repeated except that 1.23 g of p-anisidine was used instead of p-aminoacetanilide and the product was recrystallized from n-propanol whereby 2 g of the following compound as colorless plate-like crystals having a melting point of 167°–168° C. (yield 73.7%) were obtained.

CH₃O—⟨C₆H₄⟩—NHCO(CH₂)₅NH₂ · HCl

Elemental analysis: $C_{13}H_{21}N_2O_2Cl$

|  | C | H | N |
|---|---|---|---|
| Calculated (%): | 57.24 | 7.76 | 10.27 |
| Found (%): | 57.00 | 7.81 | 10.26 |

EXAMPLE 17

A 1.82 g amount of δ-aminoenanthic acid hydrochloride was suspended in 10 ml of 1,2-dichloroethane and then 1 ml of thionyl chloride and 0.5 ml of dimethylformamide were added. The mixture was stirred at room temperature for about 30 minutes to dissolve the reactants completely. A solution of 1.3 g of p-chloroaniline in 10 ml of 1,2-dichloroethane was added to the solution and the mixture was vigorously stirred about 30 minutes, and then 2.9 g of triethylamine was added to the solution and the mixture was stirred for 2.5 hours to form a slurry. The precipitate was filtered and recrystallized from 50 times the amount of water and then recrystallized from ethanol whereby 1.75 g of the following compound as colorless prismatic crystals having a melting point of 178°–180° C. (yield 60%) were obtained.

(H)

Cl—⟨C₆H₄⟩—NHCO(CH₂)₆NH₂ · HCl

Elemental analysis: $C_{13}H_{20}N_2O\ Cl$

|  | C | H | N |
|---|---|---|---|
| Calculated (%): | 53.61 | 6.92 | 9.96 |
| Found (%): | 53.56 | 7.19 | 9.58 |

EXAMPLE 18

A 3.46 g amount of θ-aminopelargonic acid was suspended in 40 ml of 1,2-dichloroethane and then 2 ml of thionyl chloride and 0.2 ml of dimethylformamide were added and the mixture was stirred at room temperature for 2 hours to give a solution. A 20 ml amount of a solution of 2.6 g of p-chloroaniline in 1,2-dichloroethane was added to the solution and the mixture was stirred at room temperature for 30 minutes, and then 2 ml of triethylamine was added to the solution. The mixture was stirred for 1 hour and then heated under reflux for 30 minutes. After cooling, the precipitate was filtered and put into about 50 times the volume of water. The mixture was heated on a boiling water bath for 1 hour and then, was concentrated and dried. The resulting residue was recrystallized from ethanol whereby 3 g of the following compound as colorless needle-like crystals having a melting point of 189°–191° C. (yield 47%) were obtained.

Cl—⟨C₆H₄⟩—NHCO(CH₂)₈NH₂ · HCl

Elemental analysis: $C_{15}H_{24}N_2OCl_2$

|  | C | H | N |
|---|---|---|---|
| Calculated (%): | 56.43 | 7.58 | 8.78 |
| Found (%): | 56.70 | 7.80 | 8.79 |

EXAMPLE 19

A 3.46 g amount of θ-aminopelargonic acid was suspended in 40 ml of 1,2-dichloroethane and 2 ml of thionyl chloride and 0.2 ml of dimethylformamide were added. The mixture was then stirred at room temperature for 2 hours to give a transparent solution. A 2.86 g amount of β-naphthylamine was added to the solution and the mixture was heated under reflux for 3 hours until the evolution of hydrogenchloride gas ceased. After cooling the solution, the precipitate was filtered and was placed into about 50 times the volume of hot water. The mixture was heated for 30 minutes on a boiling water bath and then cooled. The insoluble material was filtered and the product was dried and was recrystallized from ethanol whereby 2.65 g of the following compound as colorless amorphous crystals having a melting point of 209°–211° C. (yield 39.6%) were obtained.

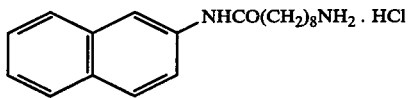

Elemental analysis: $C_{19}H_{27}N_2OCl$

|  | C | H | N |
|---|---|---|---|
| Calculated (%): | 68.14 | 8.13 | 8.37 |
| Found (%): | 68.11 | 8.29 | 8.39 |

EXAMPLE 20

A 3.74 g amount of δ-acetoamidoenanthic acid was added to a solution of 2.62 g of thionyl chloride and 0.4 ml of dimethylformamide in 40 ml of 1,2-dichloroethane. The mixture was stirred at room temperature for 1 hour and a solution of 5.2 g of p-chloroaniline in 40 ml of 1,2-dichloroethane was added to the mixture to start the reaction. The solvent was removed by distillation and the residue was washed with 2N-HCl, water, 2N-NaOH and water in that order and was dried in air, the residue was recrystallized from ethanol whereby 4.9 g of the following compound as colorless prismatic crystals having a melting point of 164°–165° C. (yield 87.5%) were obtained.

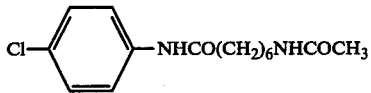

Elemental analysis: $C_{15}H_{21}N_2O_2Cl$

|  | C | H | N |
|---|---|---|---|
| Calculated (%): | 60.70 | 7.13 | 9.44 |
| Found (%): | 60.70 | 7.17 | 9.47 |

The resulting δ-acetoamidoenanthic acid p-chloroanilide was hydrolyzed in alkaline solution. The solvent was removed by distillation from the reaction mixture and the residue was washed with water and recrystallized sequentially from 0.5 N HCl, and then ethanol whereby δ-aminoenanthic acid p-chloroanilide hydrochloride as colorless prismatic crystals having a melting point of 178°–180° C. was obtained.

EXAMPLE 21

A solution of 2.3 g of m-chloroaniline and 1.55 g of triethylamine in 20 ml of 1,2-dichloroethane was vigorously stirred while cooled with ice and 30 ml of a solution of 4.2 g of ε-phthalimidocaproyl chloride in 1,2-dichloroethane was added to the solution. The mixture was stirred at room temperature for 1 hour and was kept at room temperature for one night, and 1,2-dichloroethane was removed by distillation. The residue was suspended in water and a diluted hydrochloric acid was added to it to adjust the pH to 2. The insoluble material was filtered and washed sequentially with water, an aqueous solution of sodium bicarbonate and water and was dried in air. The product was recrystallized from benzene whereby 4.9 g of 6-phthalimido-N-(3-chlorophenyl) hexanamide as colorless needle-like crystals having a melting point of 159°–160° C. (yield 88.3%) were obtained. A 1.85 g amount of the product was admixed with 20 ml of ethanol and 6 ml of 1 M-solution of hydrazine hydrate in ethanol. The mixture was heated under reflux for 7 hours and then 6 ml of 1N-HCl was added and ethanol was removed by distillation. The residue was admixed with 10 ml of water and the mixture was heated on a hot water bath at 90° C. for 1 hour. The insoluble material was filtered and filtrate was condensed under reduced pressure and the residue was admixed with acetone. The insoluble material was filtered and recrystallized from ethanol-ether whereby 0.8 g of the following compound as colorless needle-like crystals having a melting point of 112°–113° C. (yield 58%) were obtained.

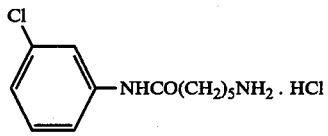
(A)

EXAMPLE 22

The process of Example 21 was repeated except that 2.2 g of p-anisidine was used instead of m-chloroaniline and the product was recrystallized from ethanol whereby 5.25 of 6-phthalimido-N-(4-methoxyphenyl) hexanamide as colorless fine needle-like crystals having a melting point of 163°–164° C. (yield 95.5%) were obtained. Thereafter 1.83 g of the intermediate were treated and the product was recrystallized from n-propanol whereby 1.05 g of the following compound as colorless plate-like crystals having a melting point of 167°–168° C. (yield 74%) were obtained.

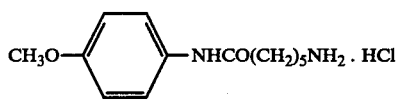

EXAMPLE 23

The process of Example 21 was repeated except that 2.5 g of p-nitroaniline were used instead of m-chloroaniline and the product was recrystallized from ethanol whereby 3.5 g of 6-phthalimido-N-(4-nitrophenyl) hexanamide as pale yellow flake-like crystals (yield of 61.4%) were obtained Thereafter, 1.91 g of the intermediate were treated and the product was recrystallized from ethanol whereby 0.85 g of the following compound as pale yellow needle-like crystals (yield 59%) was obtained.

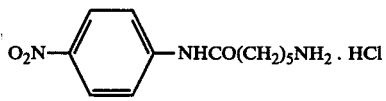

EXAMPLE 24

The process of Example 21 was repeated except that 1.92 g of p-toluidine were used instead of m-chloroaniline and the product was recrystallized from ethanol whereby 4.6 g of 6-phthalimido-N-(4-methylphenyl) hexanamide as colorless needle-like crystals having a melting point of 156°–157° C. (yield 87.5%) were obtained. A 1.75 g amount of the intermediate was treated and the product was recrystallized from ethanol-isopropyl ether whereby the following compound as colorless needle-like crystals having a melting point of 183°–184° C. (yield 70%) was obtained.

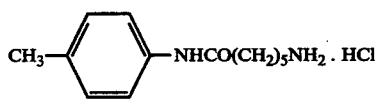

EXAMPLE 25

The process of Example 21 was repeated except that 2.58 g of β-naphthylamine were used instead of m-chloroaniline and the product was recrystallized from ethanol whereby 5.4 g of 6-phthalimido-N-(2-naphthyl) hexanamide as colorless needle-like crystals having a melting point of 156°–157° C. (yield 93%) were obtained. A 1.93 g of the intermediate was treated and the product was recrystallized from water whereby 0.93 g of the following compound as colorless needle-like crystals having a melting point of 199°–200° C. (yield 63%) was obtained.

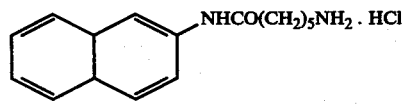

EXAMPLE 26

The process of Example 21 was repeated except that p-chloroaniline was used instead of m-chloroaniline and 1.85 g of the resulting phthalimido derivative was treated and the product was recrystallized from ethanol-acetone whereby 0.74 g of the following compound as colorless prismatic crystals having a melting point of 192°–193° C. (yield 53.3%) was obtained.

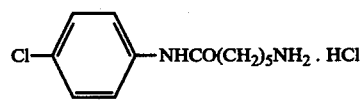

EXAMPLE 27

The process of Example 21 was repeated except that o-chloroaniline was used instead of m-chloroaniline and 1.85 g of the resulting phthalimido derivative were obtained. The product was recrystallized from ethanol-acetone whereby 0.93 g of the following compound as colorless plate-like crystals having a melting point of 132°–133° C. (yield 68%) was obtained.

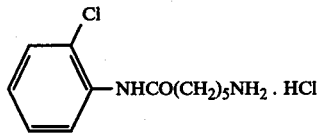

EXAMPLE 28

The process of Example 21 was repeated except that 2,6-xylidine was used instead of m-chloroaniline and 1.82 g of the resulting phthalimido derivative was treated and the product was recrystallized from ethanol-isopropyl ether whereby 0.93 g of the following compound as colorless needle-like crystals having a melting point of 149°–151° C. (yield 67%) was obtained.

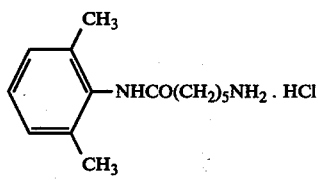

EXAMPLE 29

The process of Example 21 was repeated except that aniline was used instead of m-chloroaniline and 1.68 g of the resulting phthalimido derivative was used and the product was recrystallized from ethanol-isopropyl ether whereby 0.47 g of the following compound as colorless plate-like crystals having a melting point of 175°–176° C. (yield 38.6%) was obtained.

Having now fully described the invention, it will be apparent to one of ordinary skill in the art that many changes and modifications can be made thereto without departing from the spirit or scope of the invention as set forth herein.

What is claimed as new and intended to be covered by Letters patent is:

1. A process for producing an ω-aminoalkanoic acid arylamide having the formula

NH$_2$(CH$_2$)nCONHR wherein R represents phenyl or naphthyl which can be substituted by halogen, nitro, alkyl, alkoxy, hydroxyl, acetoamino or alkoxycarbonyl; and n is an integer of 4–8, which comprises: reacting an ω-aminoalkanoic acid of the formula NH$_2$(CH$_2$)nCOOH with thionyl chloride in a solvent; and
then reacting the resultant ω-aminoalkanoyl chloride with an aromatic amine having the formula

RNH$_2$ without separating the acid chloride from the halogenating reaction medium, to produce the corresponding alkanoic acid arylamide.

2. The process of claim 1, wherein said aromatic amine is chloroaniline, bromoaniline, nitroaniline, toluidine, xylidine, aminochlorotoluene, anisidine, aminophenol, aminoacetoanilide, ethyl aminobenzoate, aniline or naphthylamine.

3. The process of claim 1, wherein the molar ratio of the arylamine to the ω-aminoalkanoic acid chloride is in the range of 1–10: 1.

* * * * *